United States Patent
Wolf, Jr.

(10) Patent No.: US 6,794,182 B2
(45) Date of Patent: Sep. 21, 2004

(54) HYPERBARIC OXYGEN ORGAN PRESERVATION SYSTEM (HOOPS)

(76) Inventor: E. George Wolf, Jr., 3 Charterwood, San Antonio, TX (US) 78248

( * ) Notice: Subject to any disclaimer, the term of this patent is extended or adjusted under 35 U.S.C. 154(b) by 0 days.

(21) Appl. No.: 09/804,668

(22) Filed: Mar. 12, 2001

(65) Prior Publication Data

US 2002/0177117 A1 Nov. 28, 2002

Related U.S. Application Data

(60) Provisional application No. 60/188,719, filed on Mar. 13, 2000.

(51) Int. Cl.$^7$ ................................................ C12M 1/36
(52) U.S. Cl. ................................ 435/284.1; 435/286.6; 435/297.2; 435/818; 435/307.1
(58) Field of Search .......................... 435/284.1, 286.6, 435/297.2, 318, 307.1; 600/481, 508; 604/6.14; 128/202.12

(56) References Cited

U.S. PATENT DOCUMENTS

| | | |
|---|---|---|
| 3,607,646 A | 9/1971 | DeRoissart |
| 3,753,865 A | 8/1973 | Belzer |
| 3,772,153 A | 11/1973 | DeRoissart |
| 4,186,565 A | 2/1980 | Toledo-Pereyra |
| 4,837,390 A * | 6/1989 | Reneau .......................... 435/1.2 |
| 5,157,930 A | 10/1992 | McGhee |
| 5,356,771 A * | 10/1994 | O'Dell ........................ 435/284.1 |
| 5,494,822 A | 2/1996 | Sadri |
| 5,965,433 A | 10/1999 | Gardetto |
| 6,100,082 A * | 8/2000 | Hassanein ................... 435/284.1 |

\* cited by examiner

*Primary Examiner*—David A. Redding
(74) *Attorney, Agent, or Firm*—Kammer Browning PLLC

(57) ABSTRACT

A method of delivering oxygen to a biological entity comprising of dissolving oxygen into a perfusate and forcing the perfusate through the biological entity whereby substantially high levels of oxygen are available to satisfy the biological demand of the biological entity. An apparatus for supplying oxygen to a biological entity whereby substantially high levels of oxygen are available to satisfy the metabolic demand of said biological entity. An apparatus for supplying metabolic supplements to a biological entity whereby the effect of said metabolic supplement on said biological entity can be monitored. The method and apparatus keeps a biological entity such as an organ viable at a range of temperatures while in an aerobic state. This allows the study of said organ from a physiological or experimental standpoint. It allows said organ to be transplanted with little or no reperfusion injury, thus increased survivability over the prior art.

12 Claims, 2 Drawing Sheets

HYPERBARIC OXYGEN ORGAN PRESERVATION SYSTEM (HOOPS)

CROSS—REFERENCE—TO RELATED APPLICATIONS

This application claims the benefit under Title 35 United States Code §119(e) of U.S. Provisional Application No. 60/188,719 filed Mar. 13, 2000.

BACKGROUND—FIELD OF INVENTION

This invention relates to organ preservation systems, but specifically to such devices that are used to preserve an organ/biological entity for transplantation or isolated study or evaluation.

BACKGROUND—DESCRIPTION OF PRIOR ART

The invention allows an organ or a biological entity to be maintained in an active oxygenated state. This in turn greatly increases the viability of the organ while awaiting a host. It will also be used to study individual organ physiology for pharmaceuticals or any homeostatic or dynamic physiological state in which substances, chemicals, or nutrients are measured from the vascular connections.

Currently, transplant organs are stored at low temperatures to slow metabolism and thus increase the survival time of the organ and the probability of the organ being successfully transplanted. These organs still have a limited time of survival as they are in a hypoxic or low oxygen state since oxygen cannot be supplied to the tissues in adequate amounts. The survival of any organ will depend on how soon it depletes its oxygen and finally its energy stores to where even anaerobic metabolism is not possible. Organ preservation currently consists of cooling the organ to about four degrees centigrade and using preservation solutions such as UW (University of Wisconsin) or Euro-Collis (EC) solution. These still only allow limited time before the tissues are incapable of returning to an aerobic state when transplanted. Ploeg (Transplantation Feb 90) demonstrated a 24 hour median preservation time with maximum preservation time of 48 hours in a series of 257 kidney transplant patients. Stratta (transplantation Sep 90) demonstrated only a mean preservation time of 5.2 hours and 12.8 hours using EC and UW respectively in 308 liver transplant cases. One concern following a prolonged anaerobic tissue state is reperfusion injury where oxygen radicals and superoxides are formed when circulation is restored in the organ after transplantation. These radicals and superoxides in turn destroy cellular components and compromise the success of the organ surviving. This invention facilitates the organ/biological entity to remain in aerobic metabolism thus preventing reperfusion and increasing transplantation success.

The theory of using hyperbaric oxygen for hypoxic wounds has been in existence for over 30 years. Oxygen is breathed at greater than one atmosphere absolute or ATA (usually between 2 and 3 ATA). This takes advantage of normal physics by increasing the partial pressure of oxygen and thus driving oxygen into solution within the plasma other body fluids. This increases the amount of oxygen available to tissues and cells. The ability of using 100% oxygen at 3 ATA to sustain life in a bloodless animal was demonstrated in 1960 by Borema (J. Cardiovascular Surg. 1:133–146, 1960). This concept of is extended by this invention by establishing a means by which to oxygenate an isolated organ/biological entity sufficiently to meet the oxygen demand of the organ/biological entity. This is the critical novelty that separates this invention from the prior art.

U.S. Pat. Nos. 3,067,646 and 3,772,153 to De Roissart uses a complicated system to preserve the organ under hyperbaric conditions of 2 to 15 bars pressure, about 2 to 15 ATA. The system interconnects four separately pressurized containers and uses a mixture of an inert gas (preferably helium) and no more than 10% oxygen to both pressurize the system and to oxygenate the prefusate via agitation. There are many disadvantages in de Roissait's system that my invention overcomes. First my invention is a single pressurized unit, thus simpler in design and control. Second, de Roissart takes considerable time explaining how to prevent gas embolus from blocking the organ's vessels. If this were to occur, the organ would have a higher risk of failure. An embolus may occur in his system due to the inert gas coming out of solution and form bubbles within the blood vessels when the system is depressurized. This is similar to bubbles coming out of solution when a soda is opened. My system is pressurized with about 100% oxygen that is metabolically active unlike any inert gas and does not come out of solution when the system is depressurized for organ transplantation. Third, de Roissart's system relies on oxygenation of the perfusate in a nutrient fluid container. This occurs at the surface interface between the perfusate and pressurized gas mixture. This follows standard gas diffusion laws. Even though he has an agitator, this is a very inefficient means of drifting the gas into solution because of the relatively small surface area between the gas and fluid. My system overcomes this by actively using a high surface area oxygenator within the pressurized system. This dramatically increases the relative surface area between the fluid and oxygen used in my invention, thus quickly oxygenating the perfusate. My system, preferably using a minimum of 3 ATA, makes the oxygen readily available to the organ tissue at a partial pressure that is at least as high as within the lining body. This, is turn, decreases the likelihood of reperfusion injury at the time of transplantation. In order for de Roissart's system to accommodate the same tissue levels, the pressure of his system would need to be near 30 bars, twice his upper parameter! Although my system can store organs at low temperatures, it can also supply the organ with sufficient oxygen to continue normal metabolism at normal body temperature. This is not possible with de Roissart's system.

U.S. Pat. No. 4,837,390 to Reneau describes a system in which the organ is immersed in a bath of perfusate and stored in an organ preservation vessel within a hyperbaric chamber. The pressure can be up to 15 bars. Oxygenation of the perfusate is at ambient pressure (1 ATA) within a fluid reservoir using only the surface interface between the perfusate and pressurized gas. The gas is not specified, but inferred to be oxygen. My invention improves dramatically upon this. First my system overcomes this by actively using a high surface area oxygenator within the pressurized chamber vessel. This dramatically increases the relative surface area between the fluid and oxygen used in my invention, thus quickly oxygenating the perfusate. Second, the organ is actively perfused in my invention versus merely immersed in the perfusate. This is critical to the survivability of the organ as immersion alone only allows passive diffusion of oxygen and nutrients from the surface of the organ and little use of the organs vasculature. My invention actively perfuses the organ within the hyperbaric environment by pumping the perfusate from the pump and into the arterial vasculature and microvasculature. The perfusate is removed from the organ's venous vasculature via the conduit that passes through the hyperbaric chamber. By such an arrangement, the system uses the pressure within the chamber to actively transport the perfusate out of the organ and chamber because of the pressure differential. This mimics the pressure differential and thus flow of blood in a living mammal.

U.S. Pat. Nos. 4,186,565 to Toledo-Pereyra, 5,157,930 to McGhee, and 3,753,865 to Belzer establish a closed organ perfusing system that uses a pump to circulate the perfusate, but operates at ambient pressure. U.S. Pat. No. 5,965,433 to Gardetto also works within an ambient pressure environment utilizing dual pumps that push the perfusate into the organ. McGhee's system does not have a high surface area oxygenator to increase the oxygen in solution. The perfusate is returned by pumping drained perfusate from an open reservoir. In all of these systems, by only pushing the perfusate in an isobaric system, rather than pushing from the arterial side and pulling from the venous side as done in my invention, using pressure differentials, there is an increased risk of cellular edema and damage to the organ. In addition, the oxygenation and the storage of the organ is not in a high enough gas pressure and therefore does not take advantage of hyperbaric gas laws to increase oxygen into the perfusate.

U.S. Pat. No. 5,356,771 to O'Dell uses pressurized oxygen to drive an oxygen permeable membrane to pump perfusate from container one into the arterial side of an organ within another container. There is a free flow from container two back to container one. The perfusate is oxygenated from the relatively small surface area membrane. Although O'Dell mentions this as a hyperbaric perfusion, the hyperbaric forces driving oxygen into the perfusate are only present when the pressurized oxygen pushes the membrane. This is a momentary condition and only a pressure of 20 mmHg. This is near ambient pressure compared to a driving force of about 2280 mmHg in my invention. Furthermore, the pressure returns to ambient in order to complete the pumping cycle, thus the true hyperbaric forces are minimal. Again, my invention also uses a high surface area oxygenating component.

U.S. Pat. No. 5,494,822 to Sadri offers a system that controls perfusion pressure or flow rate by an intricate combination of pumps and computer controls. A unique aspect is a pump from the venous side that effectively pulls the perfusate from the organ from a mechanical means versus the gas pressure differential used in my invention. The critical difference in Sadri's system is that the oxygenation and the storage of the organ is not in a high enough gas pressure and therefore does not take advantage of hyperbaric gas laws to increase oxygen in the perfusate as happens with my invention.

The above organ preservation systems suffer from a number of disadvantages:

(a) They do not combine a high oxygen (up to 100%) hyperbaric environment with a large surface area oxygenator, thus taking advantage of physical gas laws that drive high amounts of oxygen into solution, in this case the perfusate.

(b) They do not achieve a high enough oxygen level in the perfusate to sustain normal metabolism at the normal body temperature range.

(c) They do not achieve a high enough oxygen level for a sustained period of time to avoid or minimize reperfusion injury when the organ is transplanted into the receiving host.

(d) They consist of relatively elaborate system of tubes or reservoirs that hinder the ability to remove waste products from the perfusate.

(e) They generally are manufactured with cumbersome refrigeration systems that add to the weight and bulk of the systems.

(f) They generally do not allow for the isolation study of an organ or biological entity

OBJECTS AND ADVANTAGES

Accordingly, several objects and advantages of my invention are:

(a) to provide a method in which a perfusate is oxygenated by a large surface area oxygenator within a high oxygen hyperbaric environment;

(b) to provide a method in which a perfusate is oxygenated by a large surface area oxygenator within a high oxygen hyperbaric environment sufficient enough to raise the oxygen content of the perfusate to at least 4.5 volume percent oxygen;

(c) to provide a method by which the above perfusate is delivered to an organ/biological so that said organ/biological entity can extract oxygen and nutrients;

(d) to provide a method by which the above perfusate is delivered to an organ/biological so that said organ/biological entity can extract oxygen and nutrients to remain viable from a temperature range of less than 0 to more than 40 degrees centigrade;

(e) to provide a method by which the above perfusate is delivered to an organ/biological so that said organ/biological entity can extract oxygen and nutrients to remain viable for at least 24 hours;

(f) to provide a method by which the above perfusate is delivered to an organ/biological so that said organ/biological entity such that cellular edema is minimal or non-existent;

(g) to provide a method by which said organ/biological entity's waste products are easily removed from the perfusate;

(h) to provide a method by which the perfusate can easily be sampled for tests or evaluations including, but not limited to biochemical, microbiological enzymatic, electolyte, or nutritional;

(i) to provide a method by which the above perfusate is delivered to an organ/biological so that said organ/biological entity can extract oxygen and nutrients to remain viable for transplantation with minimal reperfusion injury to the organ or entity;

(j) to provide a method by which the above perfusate is delivered to an organ/biological so that said organ/biological entity can extract oxygen and nutrients to remain viable during medical or surgical treatment, then be available for retransplantation into the original host.

Further objects and advantages of my invention will become apparent from a consideration of the drawings and ensuing description.

DRAWING FIGURES

Figure 1:
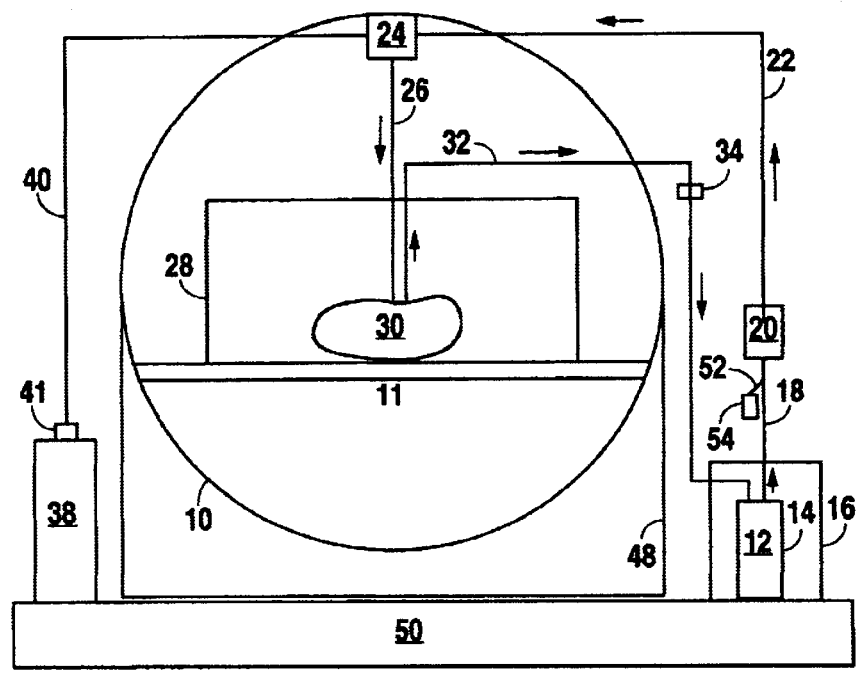
FIG. 1 is a front view of my invention.

| Reference Numerals in Drawings | |
|---|---|
| Part Name | |
| 8 | End of chamber |
| 9 | Gasket |
| 10 | Hyperbaric chamber |
| 11 | Tray |
| 12 | Perfusate |
| 14 | Perfusate container |
| 16 | Temperature control unit |
| 18 | Fluid delivery tube from bag to pump |
| 20 | Pump |
| 22 | Fluid delivery tube from pump to oxygenator |
| 24 | Oxygenator |
| 26 | Fluid delivery tube from oxygenator to organ |
| 28 | Organ container |
| 30 | Organ/biological entity |
| 32 | Fluid delivery tube from organ to perfusate bag |
| 34 | Biological filter |
| 36 | Chamber penetrator (example) |
| 38 | Pressurized gas source |
| 40 | Pressure hose |
| 41 | Gas regulator |
| 42 | Pressure gauge |
| 44 | Relief valve |
| 46 | Decompression valve |
| 48 | Cradel |
| 50 | Wheeled cart |
| 52 | Access port |
| 54 | Metabolic supplement |

SUMMARY

In accordance with this present invention an apparatus comprises a vessel capable of being pressurized, a pressurized gas, a pressure hose to deliver gas, a perfusate, a pump, an oxygenator, a plurality of fluid delivery tubes, a biological entity, and a metabolic supplement. Also in accordance with this present invention a method for supplying oxygen to a biological entity comprising of dissolving oxygen into a perfusate and forcing the perfusate through the biological entity.

DESCRIPTION

Figure 2:
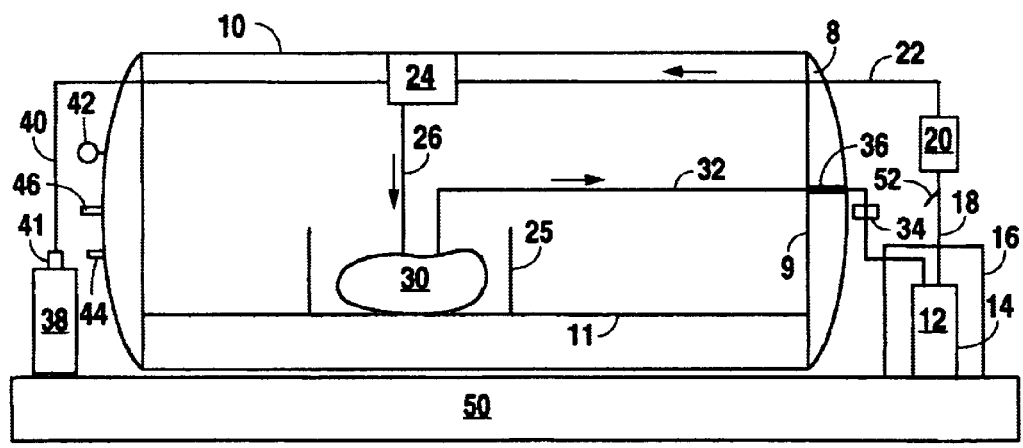
FIG. 2 is a side view of my invention.

FIG. 1 shows a frontal cross-section view of a basic version an organ preservation apparatus in accordance with the preferred embodiment of the present invention. FIG. 2 shows the side cross-section view of an organ preservation apparatus in accordance with the preferred embodiment of the present invention.

Referring to FIG. 1 and FIG. 2, there are shown the main components consisting of a hyperbaric chamber 10, perfusate 12, a perfusate container 14, a pump 20, an oxygenator 24, an organ container 28, an organ/biological entity 30, an oxygen source 38, and a cradle 48. It also shows fluid delivery tubes (18, 22, 26, 32) through which a perfusate flows, and various devices such as a pressure gauge 42, a biological filter 34, a chamber penetrator 36, a back pressure regulator/relief valve 44, an oxygen line 40, and a decompression valve 46. The entire assembly is seated on a wheeled cart 50.

Hyperbaric chamber 10 is any vessel made of, or made of a combination of steel, stainless steel, acrylic or other plastic, carbon composite or Kevlar, or any other suitable material such that the chamber can be pressurized to at least four atmospheres absolute. Its dimensions are such that its volume is sufficient to accommodate an oxygenator 24 and organ container 28 containing an organ/biological entity 30. As such, it can vary in actual size. The shape of the hyperbaric chamber may be any shape including, but not limited to spherical, cylindrical, rectangular or cubic. The preferred embodiment is a cylindrical chamber that has at least one end 8, that is sealed by, but not limited to, a hinged door or an endplate that is bolted, latched or secured in any other means along the perimeter. A gasket 9 between the chamber rim and the door or endplate is present to make a pressurized, gas-tight seal in the preferred embodiment. The chamber has a tray 11, approximately ¼ of the way from the bottom to accommodate the organ container 28 in the preferred embodiment. Said tray can be made of any suitable material and shape to substantially hold the organ container. There is a standard chamber penetrator 36 (only one identified in FIG.) for each fluid delivery tubes (18, 22, 26, 32), oxygen line 40, pressure gauge 42, decompression valve 46, relief valve 44, and any other device that requires access from outside the chamber to inside the chamber. The chamber penetrators are similar to what is known to those of ordinary skill in the art.

Perfusate 12, is a fluid containing similar electrolytes, glucose, nutrients, and other biological substances used as traditional volume expanders and preservation fluids such as, but not limited to blood, plasma, lactated Ringer's or transplantation fluids that are readily available. It may also be fluids specifically designed to carry oxygen such as, but not limited to artificial blood, fluorocarbon mixtures, and the like or a combination of any of the above. Technology is such that new fluids will be developed that will be compatible with this system and particularly suitable to the needs of newly bioengineered organs and tissues.

Perfusate container 14 in the preferred embodiment is similar to standard collapsible intravenous fluid bags but with both an outlet and inlet openings and corresponding connectors for tubing 18 and 32. This effectively allows a closed circulation system for the perfusate. A collapsible container is preferred as it allows for contraction or expansion of the container as pressure differentials occur within the system as a whole. A rigid container could be used and made of a variety of materials including, but not limited to glass, plastic, or stainless steel.

Temperature control unit 16 will depend on what the desired temperature the organ or biological entity is. In the traditional "cold storage" modality described by most prior art, it is a condition where the temperature is between 0 and 4 degrees centigrade. One method is a container that will hold the perfusate container that has sufficient room to surround the perfusate container with ice. This may be as simple as a small ice chest or insulated container. A refrigerated unit could be considered as in many of the prior art designs, however it would increase the bulk and weight of the system and is not a preferred configuration. Heating can be accomplished in a variety of ways using readily available products. This includes, but is not limited to standard IV bag warmers, heating pads, standard laboratory water baths, etc. However, the preferred embodiment for the temperature control unit uses a "thermoelectric hot/cold cooler" (THCC) commercially available, but modified with chamber penetrators to allow fluid delivery tubing 16 and 32 access to perfusate container 14 which would be placed within the THCC. This allows the temperature to be regulated to as a low as 25 degrees centigrade below ambient room temperature or heated to at least 40 degrees centigrade.

A fluid delivery tube 18 connects perfusate container 14 to pump 20. Fluid delivery tubes can be made of plastic, PVC, or other suitable material. Standard intravenous tubing can be used. The preferred tubing is that used for heart-lung bypass such as, but not limited to LAMINA by COBE Cardiovascular or Tygon by Norton Corporation. This is due to their documented endurance when used with peristaltic or roller type pumps. A similar fluid delivery tubing exists connecting pump 20 to oxygenator 24, connecting said oxygenator to organ/biological entity 30, and connecting said organ/biological entity to perfusate container 14. These tubing connecting sections are numbered 18, 22, 26, and 32 respectively. Perfusate 12 travels within the fluid delivery tubing.

Pump 20 is found in various commercial forms for intravenous or scientific research including but not limited to hydraulic, oscillating, gas pressure/diaphragm driven with one way valves, syringe, volumetric, or peristaltic or roller type. The preferred pump type is the peristaltic as perfusate 12 never comes in contact with the pump mechanism and thus contamination of the perfusate. The pump may be an individual unit or can be incorporated in a device such as, but not limited to an intravenous pump (IVAC 530 or Abbott Shaw HBO for example). The critical parameter is that it must be able to pump at a pressure higher than the pressure within the pressurized hyperbaric chamber 10; i.e. if the chamber is pressurized to 3 ATA, the pump must be able to overcome a pressure of 29.4 psi plus what is needed to perfuse the organ/biological entity.

Oxygenator 24 is in contact with pump 20 via fluid delivery tubing 22. The tubing passes through chamber end 8 within penetrator 36. The preferred embodiment penetrator 36 seals around the tubing as well as between the penetrator and the chamber such that there is an "air tight" seal even while the chamber is fully pressurized. The preferred embodiment places the penetrators through the chamber end although they may be used through any chamber surface. Alternatives to this type of penetrator includes, but is not limited to: a) a simple hole; b) a device that produces a hole in the chamber body such that tubes, wires, hoses, or any similar items can pass from outside the chamber to inside the chamber; or c) a device that produces a hole in the chamber body such that tubes, wires, hoses or similar items can be connected to either side of the device and still result in a continuous conduit. There is a plurality of penetrators sufficient for the invention.

The oxygenator is commercially obtained and may be of any type to include, but not limited to a membrane oxygenator or a capillary oxygenator. Oxygenators are similar to what is known to those of ordinary skill in the art. It is noted that most oxygenators have temperature controlled water to act as a heater or cooler of perfusate within an oxygenator. Although water could be connected to the oxygenator for this purpose, it is not the preferred embodiment for a number of reasons. First, additional penetrators would need to be used for the water lines for both enter and exit. Second, the water pressure would need to be sufficient enough to counteract the pressure within the hyperbaric chamber 10 in addition to adequate flow through the oxygenator. Third, it eliminates the ability for the system to be portable. Finally, it creates an unnecessary risk of fluid leaks within the chamber. The oxygenator is placed inside the chamber on the chamber floor, the tray, or can secured to the inside wall or the chamber by any suitable fashion.

Organ container 28 is made of, or made of a combination of steel, stainless steel, acrylic or other plastic, carbon composite or Kevlar that can be sterilized prior to use. Its dimensions are such that its volume will accommodate specific organs/biological entities 30 as mentioned below. As such, it can vary in actual size. It must however, be small enough to fit within the closed hyperbaric chamber and not interfere with the fluid delivery tubing or connections to the organ or the chamber exterior. The container can be filled with perfusate with the organ being submerged within the perfusate or the organ/biological entity can be wrapped in moist sterile surgical sponges or similar materials. The container can also be commercially obtained including those that form to the organ/entities shape.

Organ/biological entity 30 includes, but is not limited to kidney, heart, lungs, liver, spleen, bone, brain, or any other such organ, extremities or parts thereof, tissues, embryos or bioengineered or cloned organs, tissues, or embryos. Fluid delivery tube 26 connects the oxygenator 24 to the organ by cannulating the arterial vessel or other means known to those familiar in the art. Fluid delivery tube 32 that is cannulated within the organ/biological entity vein carries perfusate from organ/biological entity 30 to perfusate container 14. In doing so, it exits chamber 10 within penetrator 36, and, in the preferred embodiment, enters the temperature controller within a penetrator. In rare instances where the biological entity does not have an artery or vein, fluid delivery tube 26 is open near the top of organ container 28 such that perfusate 12 flows into organ container 28. The organ/biological entity is submerged within the perfusate in the organ container. Fluid delivery tube 32 is open near the bottom of the organ container such that the perfusate is carried to the perfusate container.

A biological filter 34 can be inserted in the customary fashion within a fluid delivery tube, preferably 32, but not necessarily, between the hyperbaric chamber and the perfusate container. This will adequately filter organ/biological entity debris in perfusate 12 prior to being recirculated to the oxygenator.

The chamber uses standard pressurized gas tanks for a pressurized gas 38 to create a hyperbaric environment inside the chamber. The pressure is controlled by a standard in line gas regulator 41. The oxygen line enters hyperbaric chamber 10 within a chamber penetrator and connects to the oxygenator using standard connections. A pressure gauge 42 is connected to a penetrator within the end of the chamber to measure the gas pressure with the chamber. A relief valve 44 set at 5 pounds per square inch above the desired chamber pressure keeps the chamber from being overpressurized. A decompression valve is connected to a penetrator so that the hyperbaric chamber can be depressurized to ambient pressure (room pressure).

If hyperbaric chamber 10 is in the preferred embodiment cylindrical shape, cradle 48, holds the chamber on a flat surface. The whole apparatus can be placed on wheeled cart 50, thus making it mobile. The apparatus can be placed and operated within a variety of vehicles, including, but not limited to ambulances, helicopters, trucks, or aircraft.

An access port 52 connected to the perfusate container or external fluid delivery tubes allows the addition of a metabolic supplement 54 to the perfusate. The metabolic supplement includes, but is not limited to nutrients, pharmaceutical agents, vitamins, and toxins.

Figure 3:
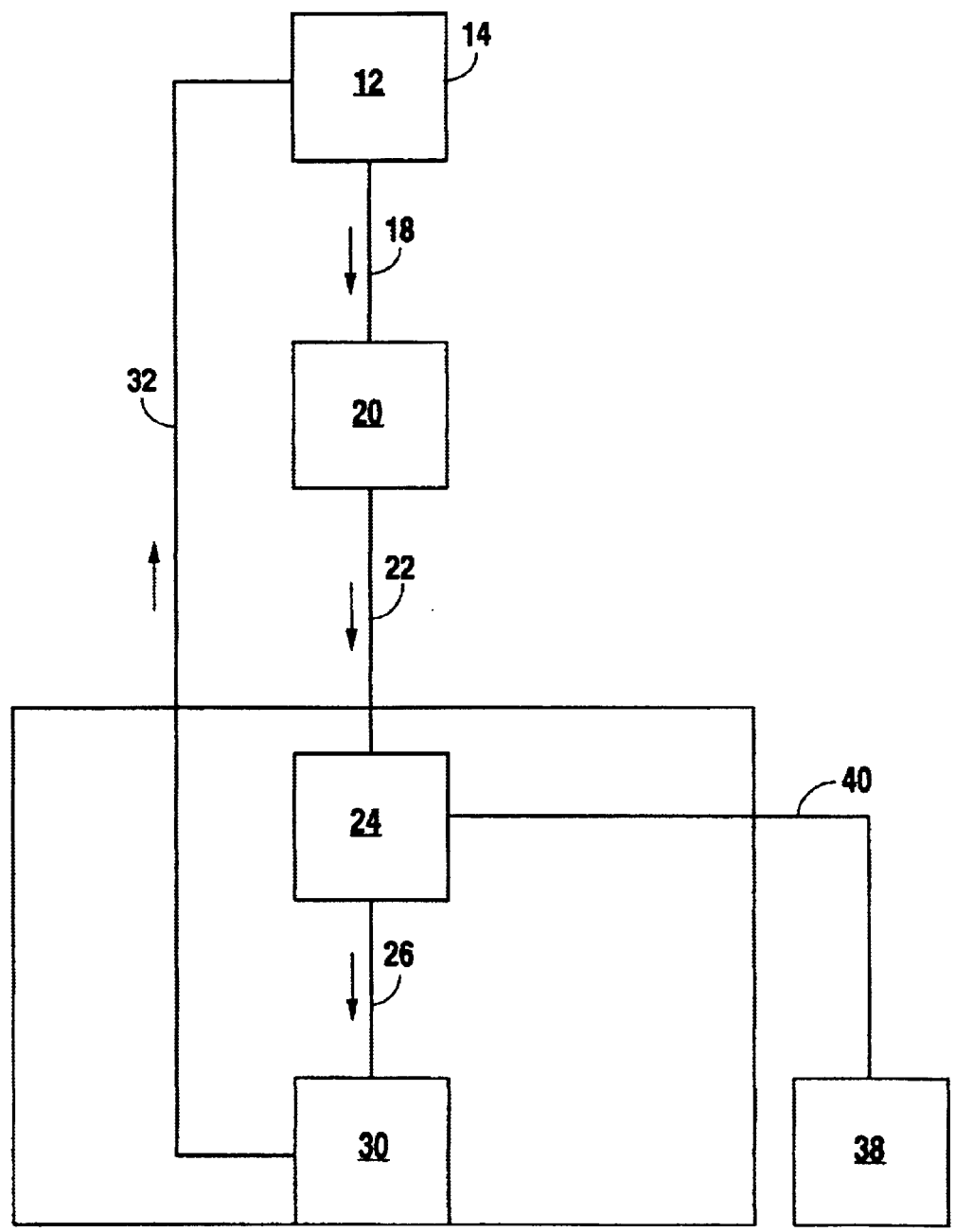
FIG. 3 is a schematic of the main components of my invention.

In reference to FIG. 3, the sequence of perfusate 12 flow through the main components above is the preferred embodiment, that is perfusate container 14, pump 20, oxygenator 24, organ/biological entity 30, and perfusate container all connected with the fluid delivery tubes (18, 22, 26, 32). Other embodiments may rearrange this sequence to include, but not limited to: a) perfusate container 14, pump 20, organ/biological entity 30, oxygenator 24, and perfusate container; b) perfusate container 14, oxygenator 24, organ/biological entity 30, pump 20, and perfusate container; or c) perfusate container 14, organ/biological entity 30, oxygenator 24, pump 20, and perfusate container.

Operation—FIGS. 1, 2

The Hyperbaric Oxygen Organ Preservation System is a self contained apparatus that will metabolically support the oxygen and nutritional requirements of organ/biological entity 30. The organ/biological entity can then be used for transplantation into a recipient host or studied per experimental protocol. A metabolic supplement can be added to the perfusate include, but not limited to meeting the nutritional demands of the organ/biological entity and determining dose response effects on the organ/biological entity. The apparatus works in the following fashion: The fluid delivery tubes 18, 22, and 26 are primed and flushed with perfusate 12 so that few, if any, bubbles remain in the tubing and oxygenator 24. This can be done by a means including, but not limited to a) connecting said tubes between perfusate container 14 and pump 20, pump 20 and oxygenator 24 and to the exit end of oxygenator 24. The other open end of fluid delivery tube 26 is placed into to organ container 28. Turning the pump on such that the fluid flows through all delivery tubes, primes the oxygenator 24, and empties into the organ container 28. An organ/biological entity is placed into the organ container. The artery, if present, is canulated or connected to the fluid delivery tube 26 via stint or other means known by those familiar with the art and secured. If an artery is not present, the fluid delivery tube 26 end is placed such that it is secured inside and near the top of organ container 28. The container is allowed to fill with perfusate 12 in which the organ/biological entity 30 can be submerged. If the organ/biological entity has a vein, fluid delivery tube 32 is connected to the organ/biological entity vein in the similar fashion as the artery. The organ is placed in the organ container and is filled with perfusate 12 until the organ is covered. Organ container 28 is placed inside of the chamber. The other end of fluid delivery tube 32 passes through the chamber within a penetrator. In the preferred embodiment biological filter 34 is connected in line in fluid delivery tube 32. Fluid delivery tube 32 passes through the side of temperature control unit 16 and is connected to perfusate container 14. This establishes a closed system. If the organ/biological entity does not have a vein, a semi-closed system can be established by allowing free venous drainage into the surrounding perfusate and the free end of fluid delivery tube 32 secured at the bottom of the perfusate filled organ container. The other end of fluid delivery tube 32 is connected to the perfusate container as above.

The chamber end is closed and secured. The chamber is pressurized with oxygen to five pounds per square inch of pressure by opening the pressurized gas source in the fashion familiar to those in the art. The gas will travel through the gas hose and the oxygenator, exiting into the closed chamber. The pump is turned on to a sufficient flow rate to insure there are no leaks. This will also flush fluid delivery tube 32 with perfusate so that few, if any, bubbles remain. The end of tube 32 can now be connected to the perfusate container. The system is checked again for leaks and that there is a flow back into the perfusate bag from fluid delivery tube 32. Any obvious leak should be corrected. If there is no leak and there still is no flow, the fluid delivery tubes should be checked for blockages or kinks and corrected. If the tubing and flow are working properly, the chamber is substantially pressurized with a gas mixture up to 100% oxygen. A pressure of at least three atmospheres is ideal. As the perfusate passes through the oxygenator under pressure, said perfusate will absorb substantially enough oxygen enough to keep the organ/biological entity's cells alive and perhaps functional. The temperature control unit heats or cools the perfusate container and perfusate within the container to the desired temperature. The perfusate, in turn heats or cools the organ/biological entity. This allows the organ/biological entity to remain viable within a wide temperature range from less than 4 degrees centigrade to at least 40 degrees centigrade. Access to the perfusate can be obtained by an access port 52 on the perfusate container or along the fluid delivery tubes similar to that seen with intravenous tubing. This allows samples to be drawn for metabolic or chemical analysis or any type of substance in proper solution. A metabolic supplement 54 can to be added to the perfusate for nutritional or pharmaceutical studies for example. A new container of perfusate can be exchanged by stopping the pump clamping fluid delivery tubes 18 and 32 near the perfusate container, disconnecting the tubing from the container, and connecting a new container to said fluid delivery tubes.

Conclusion, Ramifications, and Scope

This system has several features which make it novel. 1) It actively uses an oxygenator within a sufficiently high hyperbaric oxygen environment as an oxygen/carbon dioxide exchange interface. This allows the intracapillary and intravascular fluid to be oxygenated at a level sufficient for organ survival. 2) It has the capability to actively supply the organ with intravascular nutrients which enhance survivability; 3) If has the capability to inject pharmaceuticals and determine the dose effect on the organ within the system; 4) It has the capability to obtain intravenous samples in order to study metabolic parameters or any biochemical analysis form the circulating fluid; 5) the transplant organ can be stored at higher temperatures than traditionally used because sufficient oxygen for metabolism purposes is in solution; 6) Storage at higher temperature keeps enzyme and other metabolic functions to be near normal; 7) As the system allows near normal metabolism, the probability of organ survival past typical 24–48 hours in increased.

Although the description above contains many specificities, these should not be construed as limiting the scope of the invention but as merely providing illustrations of some of the presently preferred embodiments of this invention. The components can have various shapes, colors, or transparencies, for example.

Thus the scope of the invention should be determined by the appended claims and their legal equivalents, rather than by the examples given.

I claim:

1. A system for supplying hyperbaric oxygen to a biological entity, said system comprising:

a vessel capable of enclosing said biological entity and providing and maintaining a hyperbaric oxygen environment, said vessel having an inlet for receiving said hyperbaric oxygen into a sealed interior of said vessel; a pressure gauge, and a relief valve;

a pressurized gas source for supplying said hyperbaric oxygen to an oxygenator and the interior of the vessel said oxygenator positioned within the interior of the vessel;

a perfusate for absorbing said hyperbaric oxygen within said oxygenator;

a fluid delivery tube attached to said oxygenator; and a high pressure pump to circulate said perfusate;

whereby oxygenated perfusate is delivered under a sustained pressure environment greater than one atmosphere absolute and up to a predetermined maximum pressure to said biological entity through said fluid delivery tube.

2. The system as defined in claim 1, further including a metabolic supplement, whereby said metabolic supplement is added to said perfusate for delivery to said biological entity.

3. The system as defined in claim 2, further including means for monitoring the effect of said metabolic supplement on said biological entity.

4. The system as defined in claim 1, wherein said oxygenated perfusate contains at least 4.5 volume percent oxygen.

5. The system as defined in claim 1, further including a temperature control unit whereby the temperature at said perfusate and said biological entity can be regulated front approximately 0 degrees centigrade to approximately 40 degrees centigrade.

6. The system as defined in claim 1, wherein said perfusate contains biological entity waste products and said system further comprises a biological filter for removal of said biological entity waste products.

7. The system as defined in claim 1, further including an open perfusate container for holding said biological entity and a quantity of said perfusate within said vessel wherein said system is maintained at a pressure greater than one atmosphere absolute.

8. The system as defined in claim 1, further including a negative pressure means for circulating said perfusate from said biological entity to said oxygenator, wherein said system functions in a natural vascular manner.

9. The system as defined in claim 8, further including at least one access port in said means for circulating said perfusate wherein said access port functions in a natural venous manner.

10. The system as defined in claim 9, wherein said at least one access port permits the addition of drags or pharmaceutical agents.

11. The system as defined in claim 9, wherein said at least one access port permits the extraction of a quantity of said perfusate, wherein waste products may be removed from said perfusate and said perfusate may be analyzed.

12. The system as defined in claim 9, wherein said at least one access, port permits the addition of a quantity of said perfusate, wherein waste products may be diluted.

* * * * *